United States Patent [19]

Pfoh et al.

[11] Patent Number: 5,430,785
[45] Date of Patent: Jul. 4, 1995

[54] DETECTOR CHANNEL GAIN CALIBRATION USING FOCAL SPOT WOBBLE

[75] Inventors: Armin H. Pfoh, New Berlin, Wis.; Norbert J. Pelc, Los Altos, Calif.; Thomas L. Toth, Brookfield, Wis.

[73] Assignee: General Electric Company, Milwaukee, Wis.

[21] Appl. No.: 226,193

[22] Filed: Apr. 11, 1994

[51] Int. Cl.⁶ .................................. G01T 1/29
[52] U.S. Cl. ........................... 378/19; 378/207
[58] Field of Search ............ 378/19, 207, 98.4, 98.7, 378/98.8, 9

[56] References Cited

U.S. PATENT DOCUMENTS 4,789,930 12/1988 Sones et al. ............... 250/361 R

Primary Examiner—David P. Porta
Assistant Examiner—Don Wong
Attorney, Agent, or Firm—Quarles & Brady

[57] ABSTRACT

A 3rd generation CT system produces gain calibration factors ($\gamma$) for each channel of a detector array while a scan is being performed. Redundant views are acquired during the scan but the x-ray intensity values in the second view are shifted to the adjacent detector channel by focal spot wobbling the x-ray source. Gain calibration factors ($\gamma$) are calculated using the ratio ($\beta$) of x-ray intensity values measured at adjacent detector channels.

6 Claims, 2 Drawing Sheets

DETECTOR CHANNEL GAIN CALIBRATION USING FOCAL SPOT WOBBLE

BACKGROUND OF THE INVENTION

The present invention relates to computed tomography (CT) imaging apparatus; and more particularly, to the calibration of the x-ray detector channels.

In a current computed tomography system, an x-ray source projects a fan-shaped beam which is collimated to lie within an X-Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and detector array in a conventional "3rd generation" CT system are rotated on a gantry within the imaging plane and around the object so that the angle at which the x-ray beam intersects the object constantly changes. A group of x-ray attenuation measurements from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a cathode ray tube display. The accuracy of this reconstruction is dependent on consistent attenuation measurements of the x-rays by the detector elements throughout the scan. Changes in detector gain produce ring artifacts in the reconstructed image.

The gain stability of various x-ray detector materials and associated electronics can vary considerably. The gains of the individual detector channels in a 3 rd generation CT system are periodically calibrated by performing an "air scan" in which the x-rays unattenuated by an object are measured. System integrity depends on a relatively stable gain between these periodic calibrations. On the other hand, because the detectors receive unattenuated x-rays during each scan of an object in a 4th generation CT system, the detector channel gains can be recalibrated during each scan. As a result, some attractive x-ray detector materials like CdTe or CdWO$_4$ may perform in 4 th generation CT systems but have limited use in 3 rd generation systems because of their gain instability.

SUMMARY OF THE INVENTION

The present invention relates to a method for calibrating the detector channels on a CT system during a scan in which the x-rays are attenuated by an object. More specifically, a scan is conducted in which each view is acquired twice, but the gantry is moved and the x-ray tube focal spot position is changed between each redundant pair of view acquisitions such that the rays are shifted to the next detector in the detector array. The relative values of adjacent detector element readings are then employed to calculate gain calibrations for each detector channel relative to a reference detector channel.

A general object of the invention is to calibrate detector channel gain during each scan of an object. By moving the gantry and wobbling the focal spot the identical ray through the object is measured with two adjacent detector elements. The readings should be the same and any difference represents an incremental change in gain between the two channels. These incremental changes are accumulated throughout the detector array to arrive at absolute gain calibration corrections for each detector channel with respect to a reference detector channel.

Another object of the invention is to enable x-ray detector materials with less stable gain to be used in x-ray CT systems. The gain calibration changes can be calculated after each pair of redundant views is acquired and used to correct data acquired during the next pair of redundant views. Preferably, however, gain calibration changes will be measured over a time interval consistent with the gain stability characteristics of the particular detector material being used.

GENERAL DESCRIPTION OF THE INVENTION

Figure 4A:
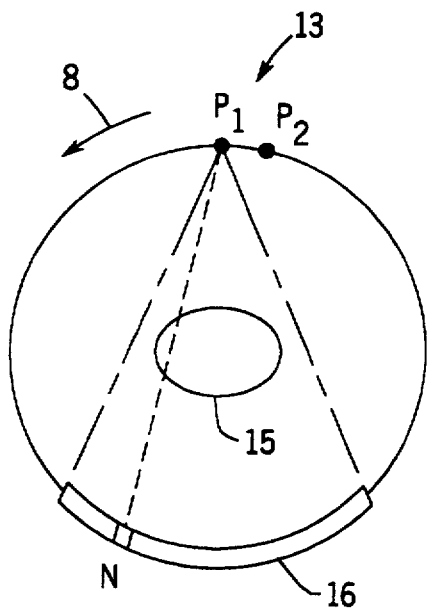
FIGS. 4A and 4B are schematic diagrams showing how redundant x-ray beams are produced for adjacent detector elements by rotating the gantry and changing the tube focal spot.
Figure 4B:
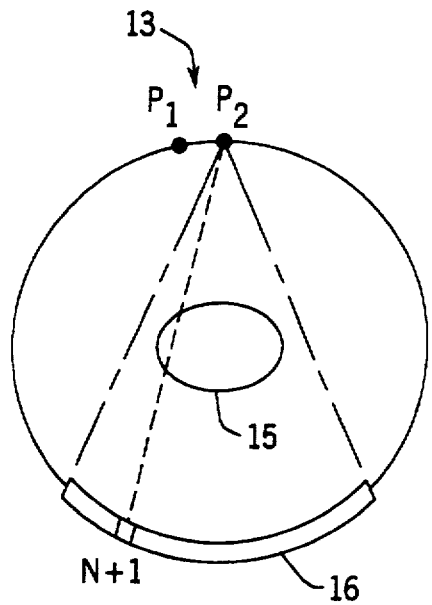

Referring particularly to FIG. 4A, the CT system according to the present invention consists of an isocentric detector array 16 and an x-ray source 13 with two well defined focal spot positions P$_2$ and P$_2$ with a spatial separation in the scan plane. The two focal spots P$_1$ and P$_2$ are activated in an alternating fashion, with only one active at any given time during the x-ray exposure, producing twice the number of views as compared to a standard CT system. The physical distance between the two focal spots is the equivalent of a gantry rotation corresponding to the displacement by one detector channel 18 in the detector array 16. The mode of operation is then as follows. Starting with an x-ray beam emanating from focal spot position P$_1$ detector element N produces an off-set corrected signal $$I_N = a_N * I \tag{1}$$

with I being the incident x-ray intensity and a$_N$ the detector gain factor. The gantry rotates in the direction indicated by arrow 8 to a position where element N+1 takes the same position as element N in the previous view, and the focal spot P$_2$ moves into the same position as P$_1$ in the previous view. An x-ray beam is produced from focal spot position P$_2$ as shown in FIG. 4B, allowing detector element N+1 to see the exact same x-ray path as element N in the previous view. Assuming a uniform beam intensity in time, the same intensity (I)

will now be incident on detector channel N+1 producing the detector reading $$I_{N+1} = \alpha_{N+1} * I. \quad (2)$$

The ratio of two adjacent detector readings from this redundant pair of views will thus be given by the ratio of the two gain factors ($\alpha_N$ and $\alpha_{N+1}$) for any two neighboring detector cells:

$$I_N/I_{N+1} = \alpha_N/\alpha_{N+1} = \beta_N \text{ "relative gain factor"} \quad (3)$$

These relative gain factors can be propagated through the entire array of M detector elements 18 to provide a gain calibration of the entire array 16 relative to a single reference detector at the edge of the array.

Let detector element M be the reference channel, the channel gain calibration $\gamma_N$ relative to M for all channels may be derived in the following way:

$$\gamma_{M-1} = \beta_{M-1} \text{ where } \beta_{M-1} = \alpha_{M-1}/\alpha_M$$
$$\gamma_{M-2} = \beta_{M-2} * \gamma_{M-1}$$
$$\gamma_{M-3} = \beta_{M-3} * \gamma_{M-2}$$
$$\cdot$$
$$\cdot$$
$$\gamma_{M-i} = \beta_{M-i} * \gamma_{M-i+1}$$

For any detector element N in the array 16, the gain calibration referenced to the end element M may thus be expressed as follows:

$$\gamma_N = \prod_{i=N}^{M-1} \beta_i = \alpha_N/\alpha_M \quad (4)$$

After applying these gain calibration factors $\gamma N$ to each detector cell (N=1, 2, ... M−1), the two redundant, and corrected readings may be summed together in order to preserve the same photon statistics as in a standard CT scan, without having to increase the x-ray source output power. For the next pair of redundant views the focal spot is deflected back to the original position P₁ and the process repeats itself.

This procedure enables one to get the same number of gain calibrations as there are number of views in a standard CT scan (approx. 1000). However, photon statistics in each pair of redundant view readings determine how many views will be combined in order to derive a statistically significant gain calibration factor for each of the detector cells 18. This procedure will at least allow one gain correction per scan, which is similar to the gain corrections currently achieved by 4 th generation CT systems.

A refinement of this method is to propagate the relative gain factor $\beta_N$ to reference detectors at both ends of the array 16. Any error in one of the relative gain measurements $\beta$ will propagate through to all subsequent calculations and deterministic errors will accumulate. These errors can be reduced by referencing each detector channel gain calibration to detector elements 18 at both ends of the array 16. Thus, in addition to referencing the detector channel gain factor $\alpha_N$ to the end element gain factor $\alpha_M$ as expressed above in equation (4), the detector channel gain factor $\alpha_N$ can be referenced to the first element in the array 16 as follows $$\alpha_1/\alpha_N = \prod_{i=1}^{N-1} \beta_i \quad (5)$$

and therefore;

$$\alpha_N/\alpha_1 = 1/\prod_{i=1}^{N-1} \beta_i \quad (6)$$

The ratio between end detector channel gains $\alpha_1/\alpha_M$ is known because they receive the same unattenuated intensity I, and another gain calibration factor $\gamma_N'$ can thus be calculated:

$$\gamma_N' = \alpha_N/\alpha_M = (\alpha_1/\alpha_M)(\alpha_N/\alpha_1) = (\alpha_1/\alpha_M)/\prod_{i=1}^{N-1} \beta_i \quad (7)$$

$\gamma_N$ and $\gamma_{N'}$ have essentially independent noise since they are calculated from different intensity ratios. Also, since the $\beta$'s are in the numerator in equation (4) and in equation (7) they are in the denominator, the deterministic errors are opposite in sign. Further, for small N $\gamma_N$ is a better estimate of the gain calibration than $\gamma_{N'}$ since fewer $\beta$'s contribute to its computation whereas the opposite is true for large N. If it is assumed that all the $\beta$'s are off by a factor c, then:

$$\gamma_N = \gamma_{N,true} c^{M-N} \quad (8)$$

while $$\gamma_{N'} = \gamma_{N,true} c^{-N} \quad (9)$$

Then, $$[(\gamma_N)^N (\gamma_{N'})^{M-N}]^{1/M} = \gamma_{N,true} \quad (10)$$

is an unbiased estimate of $\gamma_{N,true}$. For small c and small noise content, an arithmetic weighting as follows $$\gamma_{N,true} = (N/M)\gamma_N + ((M-N)/M)\gamma_{N'} \quad (11)$$

also works well. These weightings also reduce the statistical noise in the measurement as well.

In many cases it is not necessary to measure the absolute gain relative to one reference channel. Instead, the so-called channel-to-channel gain, the gain of one channel normalized to some average of nearby detector channels, is preferred. This is essentially a high pass filtered version of $\gamma_N$ which can be computed by high pass filtering the results of equations (4), (8) or (11) calculated above. In the alternative, the gain changes relative to neighboring detector channels can be calculated more directly from the set of relative gain factors $\beta_N$ by convolving them with a high pass filter kernel as will now be described.

Let $\epsilon_N$ be the fractional gain change in channel N since calibration. Thus:

$$a_N = a_N(1 + \epsilon_N) \quad (12)$$

where $a_N$ is the calibrated gain for channel N from the previous calibration. With this definition, $\epsilon_N << 1$. The rationale for this approach is that for small $\epsilon$, linear expansions should suffice. Thus:

$$\beta_N = \frac{a_N}{a_{N+1}} = \frac{a_N(1+\epsilon_N)}{a_{N+1}(1+\epsilon_{N+1})} \approx \frac{a_N}{a_{N+1}} (1+\epsilon_N - \epsilon_{N+1}) \quad (13)$$

Now, defining $\Delta_N$ to be the difference in fractional gain change between channels N and N+1, we have:

$$\Delta_N = \epsilon_N - \epsilon_{N+1} = \beta_N \frac{a_{N+1}}{a_N} - 1 \quad (14)$$

Note that the pre-calibrated gains appear as ratios. If the detector channels have similar enough gain one can assume $a_N/a_{N+1} = 1$ and thereby put all the gain difference into $\Delta_N$.

What we desire are the $\epsilon$'s. The advantage of obtaining the $\Delta$'s from the $\beta$'s is that the $\Delta$'s are linear in the $\epsilon$'s, in fact the $\Delta$'s are simply the $\epsilon$'s convolved with a filter $f = \delta(0) - \delta(1)$ where $\delta$ is a Dirac delta function. Thus, from the $\Delta$'s which are computed using equation (14), the $\epsilon$'s can be found by convolving with the inverse of f, $f^{-1}$, and the $\alpha$'s can be computed using equation (12).

For high passed (channel-to-channel) gain changes we desire the convolution of the $\epsilon$'s with some high pass filter g. One recognizes that the $\Delta$'s are already a high passed version of $\epsilon$; the only problem is that the high pass filter $f = \delta(0) - \delta(1)$ is not necessarily the filter g we want. It can be shown that the desired high passed gains $\gamma_N$ can be directly computed from the $\Delta$'s by a convolution with a filter that is a modified version of the desired high pass filter g. The new filter "k" is in fact one term shorter than g. That is if the desired high pass filter g is a seven point high pass filter kernel ($g_3$, $g_2$, $g_1$, $g_0$, $g_1$, $g_2$, $g_3$), then the new filter k is a six point high pass filter in which the values are calculated as follows:

$k_0 = g_3$ $k_1 = g_3 + g_2$ $k_2 g_3 + g_2 + g_1$ $k_3 = g_3 + g_2 + g_1 + g_0$ $k_4 + g_3 + g_2 + 2g_1 + g_0$ $k_5 = g_3 + 2g_2 + 2g_1 + g_0$

Thus the desired gain adjustments are calculated by convolving the gain changes between channels $\Delta_N$ with the filter k:

$$\gamma_N^1 = \Delta_N \otimes k \quad (16)$$

The so-called calibration air-scan is not entirely eliminated, when the present invention is employed since it is required for CT systems with a bow-tie beam filter in order to characterize the bow-tie shape relative to the two different focal spot positions $P_1$ and $P_2$. The bow-tie filter causes a difference in the incident x-ray flux (I) for the two adjacent readings $I_N$ and $I_{N+1}$ due to different x-ray path lengths through the bow-tie filter. This difference can be characterized by means of an air calibration scan with no object in the scan path. Variations in the x-ray source output flux over time is also corrected by means of a reference detector at the end of the array 16 that is exposed to the unattenuated x-ray beam at all times.

DETAILED OF THE PREFERRED EMBODIMENT

Figure 1:
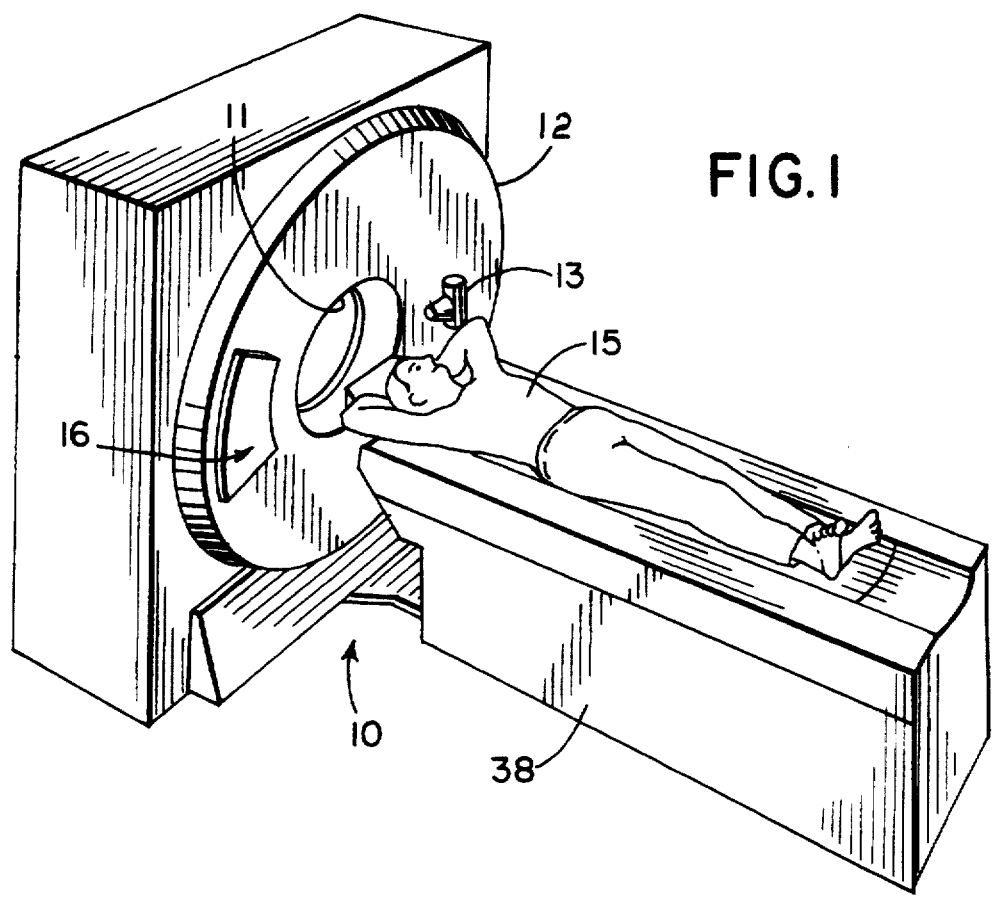
FIG. 1 is a pictorial view of a CT imaging system in which the present invention may be employed.
Figure 2:
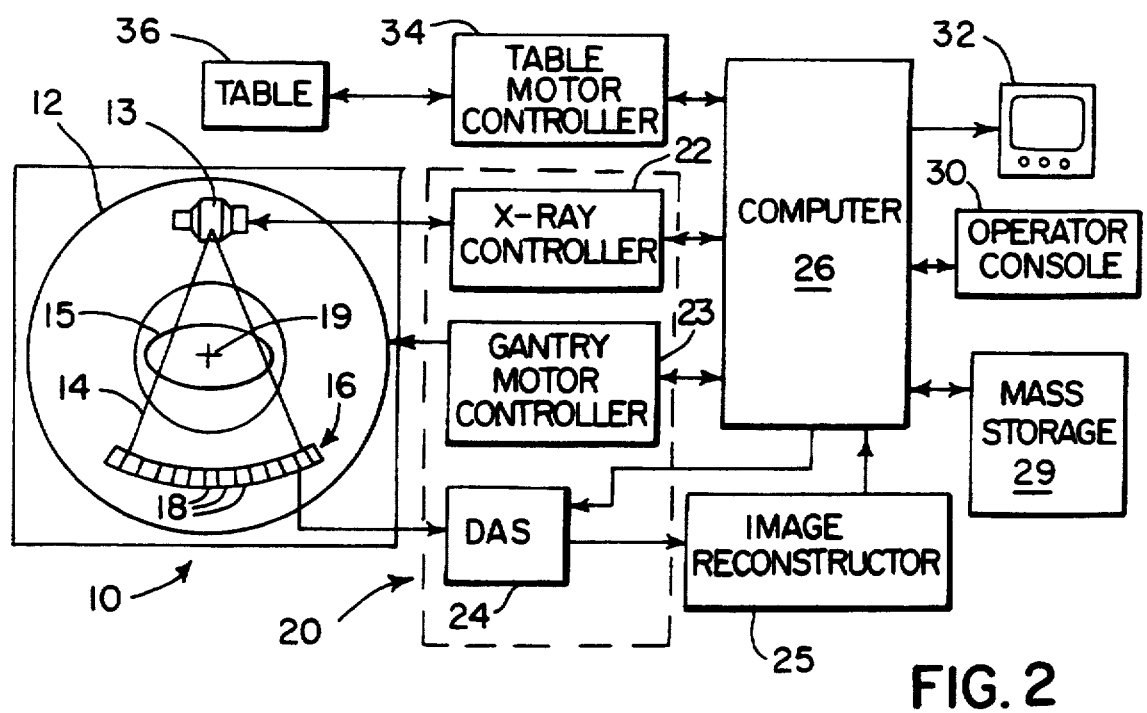
FIG. 2 is a block schematic diagram of the CT imaging system.

With reference to FIGS. 1 and 2, a computed tomography (CT) imaging system 10 includes a gantry 12 representative of a "third generation" CT scanner. Gantry 12 has an x-ray source 13 that projects a cone beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15.

The rotation of the gantry and the operation of the x-ray source 13 are governed by a control mechanism 20 of the CT system. The control mechanism 20 includes an x-ray controller 22 that provides power, timing signals, and focal spot position control for the x-ray source 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction according to the method of the present invention. The reconstructed image is applied as an input to a computer 26 which stores the image in a mass storage device 29.

The computer 26 also receives commands and scanning parameters from an operator via console 30 that has a keyboard. An associated cathode ray tube display 32 allows the operator to observe the reconstructed image and other data from the computer 26. The operator supplied commands and parameters are used by the computer 26 to provide control signals and information to the DAS 24, the x-ray controller 22 and the gantry motor controller 23. In addition, computer 26 operates a table motor controller 34 which controls a motorized table 36 to position the patient 15 in the gantry 12.

Figure 3:
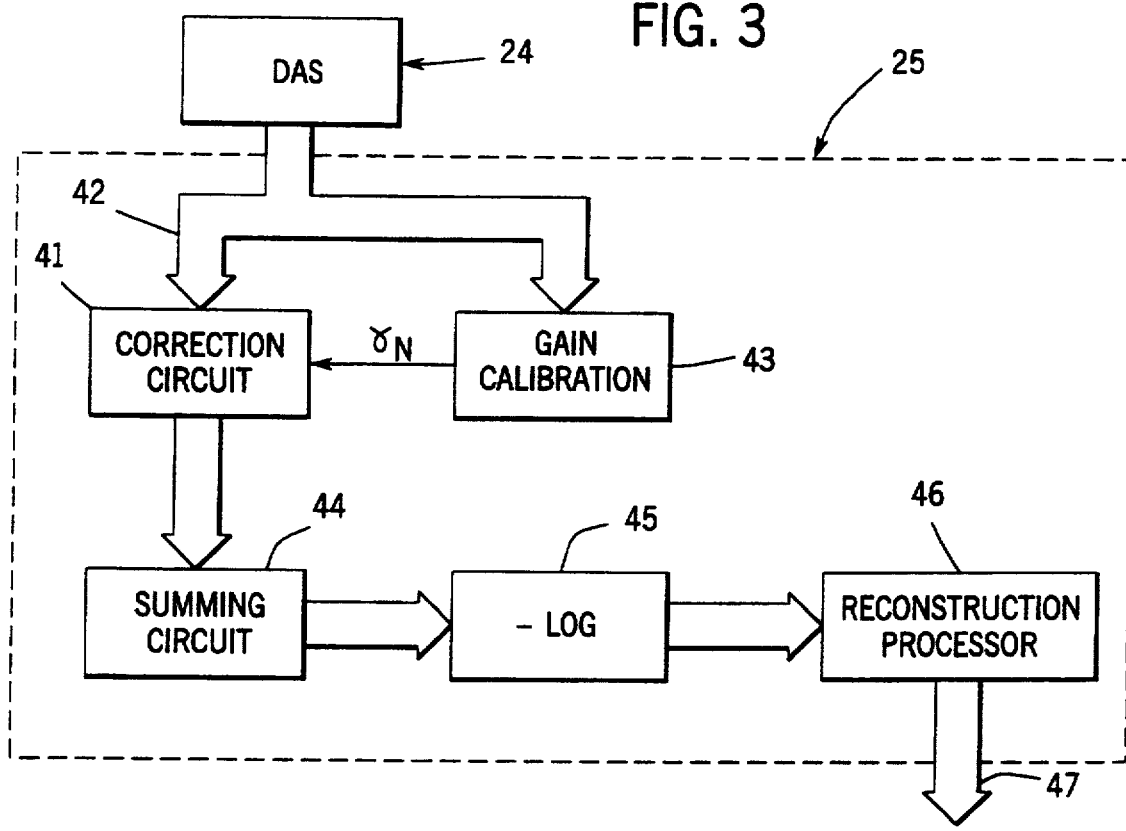
FIG. 3 is an electrical block diagram of an image constructor which forms part of the CT system of FIG. 2.

Referring particularly to FIG. 3, as each view is acquired during a scan a set of scan data values which indicate the number of x-ray photons sensed by the detector elements 18 are conveyed by the DAS 24 to the image constructor 25. These intensity values I are produced by the detectors 18 and are subject to changes in detector channel gain which must be corrected along with other errors in a correction circuit 41. The intensity values are thus applied through a bus 42 to the correction circuit 41 which adjusts the scan data for variations in detector and DAS channel gains, dark current offsets and beam hardening. The same scan data is also conveyed through bus 42 to a gain calibration circuit 43 which executes the above described equations (4), (7) and

(10) to produce gain calibration values $\gamma_N$ to the correction circuit 41. After correction by the circuit 41, corrected scan data from redundant pairs of views is combined at summing circuit 44 and the resulting scan data is processed in a well known manner by taking the negative of its logarithm at 45 to produce a single projection profile for each view. These projection profiles are applied to a reconstruction processor 46 which filters and back projects them to form slice images that are output at 47 to the computer 26.

The gain calibration circuit 43 makes its calculations as described above to produce a set of gain calibration factors $\gamma_N$ after each pair of redundant views are acquired during the scan. While these values $\gamma_N$ can be applied to the correction circuit 41 and used to change the gain corrections made to each pair of redundant views, in the preferred embodiment the sets of values $\gamma_N$ are examined and combined to form the best estimate of the true gain ratios, new gain calibration factors $\gamma_N$ are output to the correction circuit 41.

It should be apparent to those skilled in the art that many variations can be made from the preferred embodiments described above without departing from the spirit of the invention. For example, the detector array in the preferred embodiment is concentric, or centered, about the axis of rotation 19. The invention may also be employed in systems where the detector array is concentric about the focal spots in the x-ray tube 13, as long as the arc subtended by the detector array is not too large.

We claim:

1. In a CT system having an x-ray source which is revolved around an object to be imaged and a detector array comprised of a set of detector channels for producing a corresponding set of x-ray intensity values at each of a succession of views as the x-ray source revolves, a method for producing detector channel gain calibration factors ($\gamma$), the steps comprising:
   a) acquiring a first set of x-ray intensity values with x-rays emanating from a first focal spot position ($P_1$) in the x-ray source;
   b) rotating the x-ray source to a position for acquiring the next view of the object;
   c) acquiring a second set of x-ray intensity values with x-rays emanating from a second focal spot position ($P_2$) in the x-ray source which is displaced in the plane of x-ray source revolution such that the second set of x-ray intensity values are redundant of the first set of x-ray intensity values;
   d) calculating the relative gain factor ($\beta$) of adjacent detector channels by taking the ratio of the x-ray intensity values acquired in steps a) and c); and
   e) calculating a gain calibration factor ($\gamma$) for each detector channel which relates the gain of said detector channel to a reference detector channel in the detector array using the relative gain factors ($\beta$) calculated in step d).

2. The method as recited in claim 1 in which the detector array revolves around the object along with the x-ray source.

3. The method as recited in claim 1 in which the reference detector channel is located at one end of the detector array 16.

4. The method as recited in claim 1 in which the gain calibration factor ($\gamma$) calculated in step e) also relates the gain of each detector channel to a second reference detector channel located at a second end of the detector array using the relative gain factors ($\beta$) calculated in step d).

5. The method as recited in claim 1 in which steps a), b) and c) are repeated throughout the revolution of the x-ray source around the object to acquire a redundant set of x-ray intensity values at each view of the object.

6. In a CT system having an x-ray source which is revolved around an object to be imaged and a detector array comprised of a set of detector channels for producing a corresponding set of x-ray intensity values at each of a succession of views as the x-ray source revolves, a method for producing detector channel gain calibration factors ($\gamma$), the steps comprising:
   a) acquiring a first set of x-ray intensity values with x-rays emanating from a first focal spot position ($P_1$) in the x-ray source;
   b) rotating the x-ray source to a position for acquiring the next view of the object;
   c) acquiring a second set of x-ray intensity values with x-rays emanating from a second focal spot position ($P_2$) in the x-ray source which is displaced in the plane of x-ray source revolution such that the second set of x-ray intensity values are redundant of the first set of x-ray intensity values;
   d) calculating the difference in gain changes ($\Delta$) between adjacent detector channels by taking the ratio of the x-ray intensity values acquired in steps a) and c); and
   e) calculating a gain calibration factor ($\gamma$) for each detector channel by convolving the difference in gain change values ($\Delta$) with a filter kernel k.

* * * * *